(12) United States Patent
Janbakhsh

(10) Patent No.: US 7,904,193 B2
(45) Date of Patent: Mar. 8, 2011

(54) SYSTEMS AND METHODS FOR PROVIDING CUSTOM MASKS FOR USE IN A BREATHING ASSISTANCE SYSTEM

(75) Inventor: Mahmoud Janbakhsh, San Ramon, CA (US)

(73) Assignee: Nellcor Puritan Bennett LLC, Boulder, CO (US)

( * ) Notice: Subject to any disclaimer, the term of this patent is extended or adjusted under 35 U.S.C. 154(b) by 679 days.

(21) Appl. No.: 11/536,993

(22) Filed: Sep. 29, 2006

(65) Prior Publication Data

US 2008/0078396 A1    Apr. 3, 2008

(51) Int. Cl.
G06F 19/00   (2011.01)
A62B 18/02   (2006.01)

(52) U.S. Cl. ............ 700/118; 700/117; 128/206.21
(58) Field of Classification Search ............ 700/117, 700/119, 118; 128/206.21
See application file for complete search history.

(56) References Cited

U.S. PATENT DOCUMENTS

| | | | |
|---|---|---|---|
| 5,647,357 A | 7/1997 | Barnett et al. | 128/206.24 |
| 5,755,219 A | 5/1998 | Thornton | 128/201.18 |
| 5,832,918 A | 11/1998 | Pantino | 128/205.25 |
| 5,884,624 A | 3/1999 | Barnett et al. | 128/206.24 |
| 5,954,048 A | 9/1999 | Thornton | 128/201.18 |
| 6,209,542 B1 | 4/2001 | Thornton | 128/206.29 |
| 6,247,926 B1 | 6/2001 | Thornton | 433/48 |
| 6,305,376 B1 | 10/2001 | Thornton | 128/848 |
| 6,374,824 B1 | 4/2002 | Thornton | 128/201.26 |
| 6,397,847 B1 | 6/2002 | Scarberry et al. | 128/206.24 |
| 6,405,729 B1 | 6/2002 | Thornton | 128/848 |
| 6,464,924 B1 | 10/2002 | Thornton | 264/331.12 |
| 6,494,206 B1 | 12/2002 | Bergamaschi et al. | 128/206.24 |
| 6,516,805 B1 | 2/2003 | Thornton | 128/848 |
| 6,571,798 B1 | 6/2003 | Thornton | 128/206.21 |
| 6,675,802 B1 | 1/2004 | Thornton | 128/206.29 |
| 6,701,927 B2 | 3/2004 | Kwok et al. | 128/207.13 |
| 6,728,589 B1 | 4/2004 | Delache et al. | 700/117 |
| 6,843,249 B2 | 1/2005 | Bergamaschi et al. | 128/206.24 |
| 6,857,428 B2 | 2/2005 | Thornton | 128/206.21 |
| 6,895,965 B2 | 5/2005 | Scarberry et al. | 128/206.24 |
| 7,069,933 B2 | 7/2006 | Kwok et al. | 128/206.24 |
| 2003/0131852 A1* | 7/2003 | Shafer et al. | 128/206.21 |

(Continued)

FOREIGN PATENT DOCUMENTS

WO    WO 00/59567    * 10/2000

(Continued)

OTHER PUBLICATIONS

"Soft Elastomeric Materials for Fused Deposition Modeling" [Online], XP002474641, URL:http://www-rp.me.vt.edu/bohn/rp/elastomer/masks.html, 1 page, Aug. 4, 1997.

(Continued)

Primary Examiner — Ramesh B Patel
Assistant Examiner — Steven R Garland

(57) ABSTRACT

A method for fabricating a facial seal for use in a breathing assistance system is provided. The method includes capturing one or more images of a patient's face. The method further includes translating the one or more images into a set of data representing a three-dimensional structure of at least a portion of the patient's face and fabricating a facial seal to substantially conform to the patient's face based at least on the set of data, including fabricating at least a portion of the facial seal using rapid prototyping or a subtractive manufacturing technique. A method for selecting a facial seal for a breathing assistance system is also disclosed.

6 Claims, 7 Drawing Sheets

U.S. PATENT DOCUMENTS

| | | | |
|---|---|---|---|
| 2004/0133604 A1* | 7/2004 | Lordo | 707/104.1 |
| 2006/0023228 A1 | 2/2006 | Geng | 356/601 |
| 2006/0027237 A1 | 2/2006 | Sleeper et al. | 128/207.13 |
| 2006/0076018 A1 | 4/2006 | Barnett et al. | 128/206.24 |
| 2006/0235877 A1* | 10/2006 | Richard et al. | 707/104.1 |
| 2008/0006273 A1* | 1/2008 | Thornton | 128/206.21 |

FOREIGN PATENT DOCUMENTS

WO    WO 2005/118401 A1    12/2005

OTHER PUBLICATIONS

International Search Report with Written Opinion PCT/US2007/079716, 18 pages, Mailing date Apr. 15, 2008.

* cited by examiner

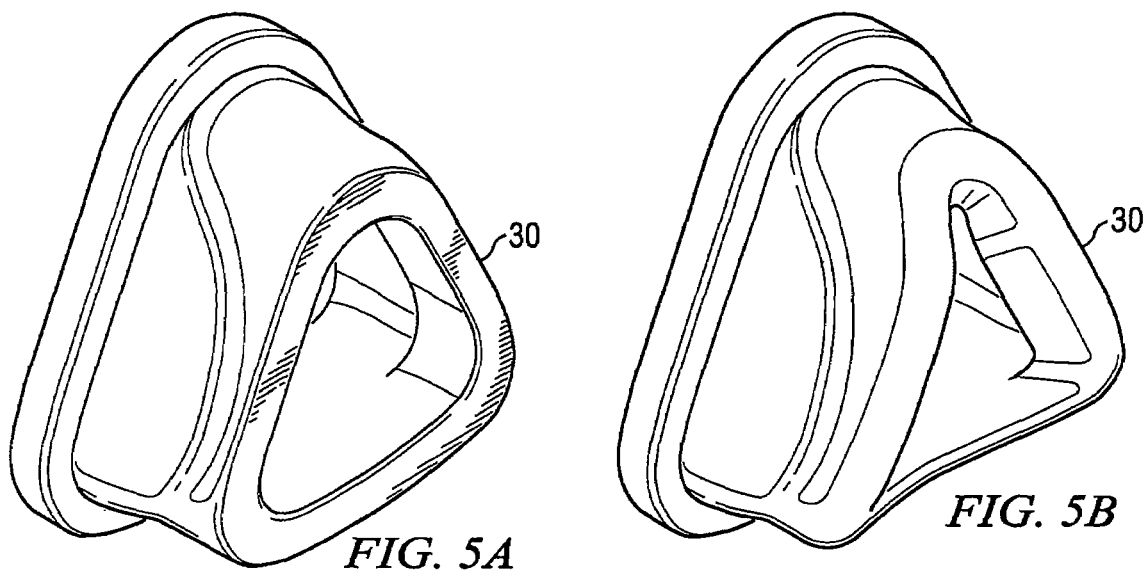
*FIG. 5A*  *FIG. 5B*
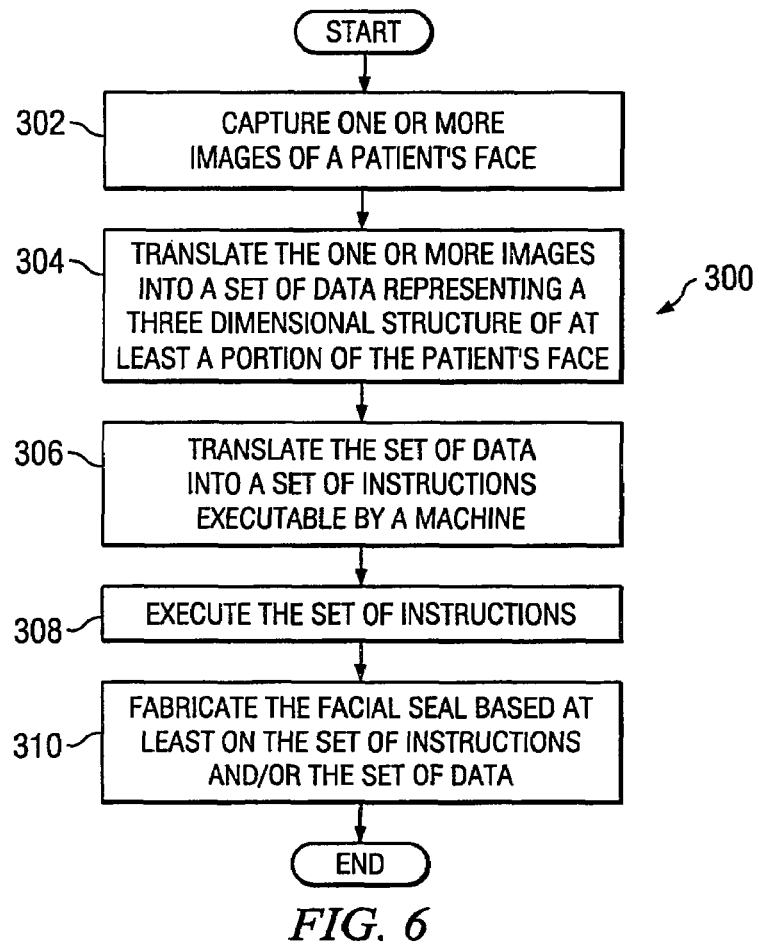
*FIG. 6*

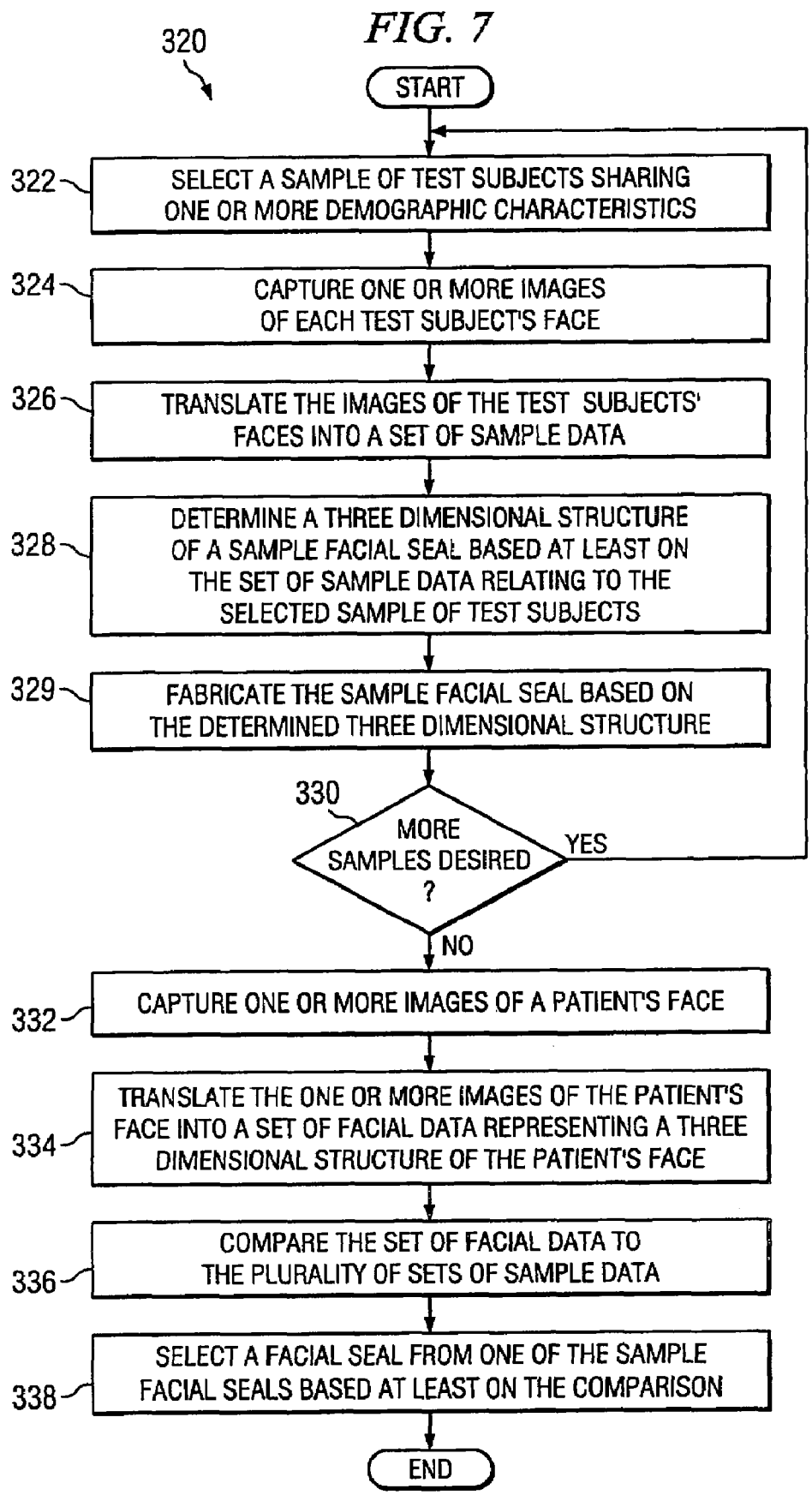

SYSTEMS AND METHODS FOR PROVIDING CUSTOM MASKS FOR USE IN A BREATHING ASSISTANCE SYSTEM

TECHNICAL FIELD

The present disclosure relates generally to the field of breathing assistance systems, e.g., systems and methods for providing custom masks for use in a breathing assistance system.

BACKGROUND

In recent years, continuous positive airway pressure (CPAP) therapy has become a common prescription for individuals suffering from sleep apnea and/or other breathing ailments. Such therapy may involve placement of a nose or face mask on the subject during sleep, while positive pressure air is continuously delivered to the subject through the mask. The positive pressure air may be delivered to the patient's upper airway to prevent the upper airway tissues from collapsing during sleep, thus reducing the occurrence and/or severity of sleep apnea.

However, conventional masks have several disadvantages. For example, conventional masks may form a poor seal with the face of a patient, because many mask assemblies conform to only standard sizes and shapes. Second, conventional masks may not account for differences in the sizes or shapes of the facial features of different patients, thus causing discomfort or pain. Third, because of the poor seals or fits often associated with conventional masks, the mask may not stay in place, and may shift or move.

SUMMARY

In accordance with one embodiment of the present disclosure, a method for fabricating a facial seal for use in a breathing assistance system is provided. The method includes capturing one or more images of a patient's face. The method further includes translating the one or more images into a set of data representing a three-dimensional structure of at least a portion of the patient's face and fabricating a facial seal to substantially conform to the patient's face based at least on the set of data, including fabricating at least a portion of the facial seal using rapid prototyping.

In accordance with yet another one embodiment of the present disclosure, a method for fabricating a facial seal for use in a breathing assistance system is provided. The method includes capturing one or more images of a patient's face. The method also includes translating the one or more images into a set of data representing a three-dimensional structure of at least a portion of the patient's face, and based at least on the set of data, using a subtractive technique to create a three-dimensional pattern of at least a portion of a facial seal, the three-dimensional pattern substantially conforming to the patient's face.

In accordance with another embodiment of the present disclosure, a method for selecting a facial seal for use in a breathing assistance system is provided. The method includes capturing one or more images of a patient's face. The method further includes translating the one or more images of the patient's face into a set of facial data representing a three-dimensional structure of the portion of at least a portion of the patient's face and automatically selecting a particular one of a plurality of sample facial seals having different predetermined shapes, the particular facial seal selected to substantially conform to the patient's face based at least on the set of facial data.

In accordance with yet another embodiment of the present disclosure, a system for fabricating a facial seal for use in a breathing assistance system includes an imaging system, a computer, and a rapid prototyping machine. The imaging system may be operable to capture one or more images of a patient's face. The computer may be operable to translate the one or more images into a set of data representing a three-dimensional structure of at least a portion of the patient's face. The rapid prototyping machine may be operable to fabricate the facial seal to substantially conform to the patient's face based at least on the set of data.

In accordance with yet another embodiment of the present disclosure, a system for fabricating a facial seal for use in a breathing assistance system includes an imaging system, a computer, and a machine. The imaging system may be operable to capture one or more images of a patient's face. The computer may be operable to translate the one or more images of the patient's face into a set of data representing the three-dimensional structure of the portion of the patient's face. The machine may be operable to create, using a subtractive technique, a three-dimensional pattern in at least a portion of a facial seal, the three-dimensional pattern substantially conforming to the patient's face.

In accordance with yet another embodiment of the present disclosure, a system for fabricating a facial seal for use in a breathing assistance system includes an imaging system and a computer. The imaging system may be operable to capture one or more images of a patient's face. The computer may be operable to translate the one or more images of the patient's face into a set of facial data representing a three-dimensional structure of at least a portion of the patient's face and automatically select a particular one of a plurality of sample facial seals having different predetermined shapes, the particular facial selected to substantially conform to the patient's face based at least on the set of facial data.

In accordance with yet another embodiment of the present disclosure, a method for fabricating a facial seal for use in a breathing assistance system is disclosed. The method includes obtaining a set of data representing a three-dimensional structure of at least a portion of a patient's face. The method further includes fabricating a facial seal to substantially conform to the patient's face based at least on the set of data, including fabricating at least a portion of the facial seal using rapid prototyping.

In accordance with yet another embodiment of the present disclosure, a method for fabricating a facial seal for use in a breathing assistance system is disclosed. The method includes obtaining a set of data representing a three-dimensional structure of at least a portion of a patient's face. The method further includes using a subtractive technique to create a three-dimensional pattern of at least a portion of a facial seal based at least on the set of data, the three-dimensional pattern substantially conforming to the patient's face.

In accordance with yet another embodiment of the present disclosure, a method for fabricating a facial seal for use in a breathing assistance system is disclosed. The method includes obtaining a set of data representing a three-dimensional structure of at least a portion of a patient's face. The method further includes automatically selecting a particular one of a plurality of sample facial seals having different predetermined shapes, the particular facial seal selected to substantially conform to the patient's face based at least on the set of facial data.

In accordance with yet another embodiment of the present disclosure, a facial seal includes a first side, a second side and a passageway. The first side may have a first seal opening, and the first side may be configured to provide a seal against a patient's face, the second side may have a second seal opening. The passageway may extend between the first seal opening and the second seal opening and may be operable to deliver breathing gas to a patient. The facial seal may be fabricated by capturing one or more images of a patient's face, translating the one or more images into a set of data representing a three-dimensional structure of at least a portion of the patient's face, and fabricating a facial seal to substantially conform to the patient's face based at least on the set of data, including fabricating at least a portion of the facial seal using rapid prototyping.

In accordance with yet another embodiment of the present disclosure, a facial seal includes a first side, a second side and a passageway. The first side may have a first seal opening, and the first side may be configured to provide a seal against a patient's face, the second side may have a second seal opening. The passageway may extend between the first seal opening and the second seal opening and may be operable to deliver breathing gas to a patient. The facial seal may be fabricated by capturing one or more images of a patient's face, translating the one or more images into a set of data representing a three-dimensional structure of at least a portion of the patient's face, and based at least on the set of data, using a subtractive technique to create a three-dimensional pattern of at least a portion of the facial seal, the three-dimensional pattern substantially conforming to the patient's face.

In accordance with yet another embodiment of the present disclosure, a mask assembly for use in a breathing assistance system may include one of more gas delivery conduits and a patient interface. The one or more gas delivery conduits may be configured to receive gas from a delivery source. The patient interface may be configured to communicate gas from the one or more gas delivery conduits to a patient. The patient interface may include a facial seal configured to provide a seal against a patient's face and a seal support configured to support the facial seal. The facial seal may be fabricated by capturing one or more images of a patient's face, translating the one or more images into a set of data representing a three-dimensional structure of at least a portion of the patient's face, and fabricating a facial seal to substantially conform to the patient's face based at least on the set of data, including fabricating at least a portion of the facial seal using rapid prototyping.

In accordance with yet another embodiment of the present disclosure, a mask assembly for use in a breathing assistance system may include one of more gas delivery conduits and a patient interface. The one or more gas delivery conduits may be configured to receive gas from a delivery source. The patient interface may be configured to communicate gas from the one or more gas delivery conduits to a patient. The patient interface may include a facial seal configured to provide a seal against a patient's face and a seal support configured to support the facial seal. The facial seal may be fabricated by capturing one or more images of a patient's face, translating the one or more images into a set of data representing a three-dimensional structure of at least a portion of the patient's face, and based at least on the set of data, using a subtractive technique to create a three-dimensional pattern of at least a portion of the facial seal, the three-dimensional pattern substantially conforming to the patient's face.

In accordance with yet another embodiment of the present disclosure, a system for fabricating a facial seal for use in a breathing assistance system includes imaging means for capturing one or more images of a patient's face, translation means for translating the one or more images into a set of data representing a three-dimensional structure of at least a portion of the patient's face, and rapid prototyping means for fabricating the facial seal to substantially conform to the patient's face based at least on the set of data.

BRIEF DESCRIPTION OF THE DRAWINGS

FIGS. 5A-5B illustrate various stages of fabrication of a facial seal using a subtractive technique, according to one embodiment of the disclosure;

FIG. 6 illustrates an example method for fabricating a facial seal, according to some embodiments of the disclosure; and FIG. 7 illustrates an example method for selecting a facial seal from a plurality of sample facial seals, according to some embodiments of the disclosure.

DETAILED DESCRIPTION OF THE DRAWINGS

Selected embodiments of the disclosure may be understood by reference, in part, to FIGS. 1-7, wherein like numbers refer to same and like parts. The present disclosure relates generally to patient interfaces (e.g., masks) for breathing assistance systems (e.g., ventilators, CPAP devices, or BiPAP devices). A method for fabricating a facial seal for use in a breathing assistance system may include capturing one or more images of a patient's face, translating the one or more images into a set of data representing a three-dimensional structure of at least a portion of the patient's face, and fabricating a facial seal to substantially conform to the patient's face based at least on the set of data. In some embodiments, the facial seal may be fabricated using rapid prototyping (e.g., selective laser sintering, fused deposition modeling, three-dimensional laser printing, or laminated object manufacturing). In the same or alternative embodiments, the facial seal may be fabricating using a subtractive manufacturing technique (e.g., laser ablation, chemical removal, and mechanical cutting).

In addition, a method for selecting a facial seal for a particular patient may include capturing one or more images of the patient's face, translating the one or more images into a set of facial data representing a three-dimensional structure of at least a portion of the patient's face, and automatically selecting a particular facial seal from a plurality of sample facial seals to substantially conform to the patient's face based at least on the set of facial data.

Figure 1:
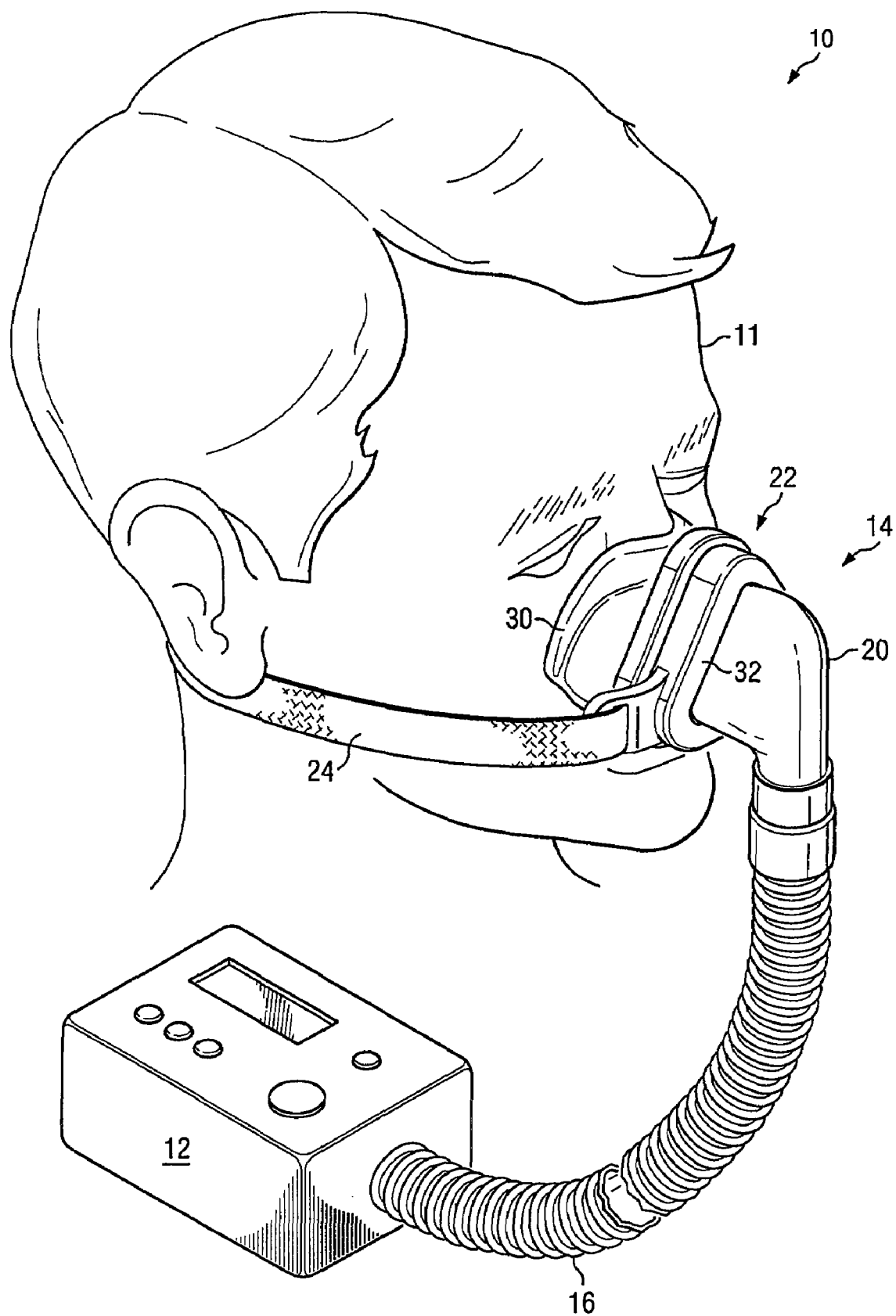
FIG. 1 illustrates an example breathing assistance system for providing breathing assistance to a patient, according to one embodiment of the disclosure.

FIG. 1 illustrates an example breathing assistance system 10, according to one embodiment of the disclosure. Breathing assistance system 10 may be generally configured to provide breathing assistance (e.g., providing ventilation and/or treating an apnea or other breathing condition) to a patient 11. Breathing assistance system 10 may include a gas delivery system 12, a mask apparatus 14, and a connection system 16 between gas delivery system 12 and mask apparatus 14.

Gas delivery system 12 may include any device or devices configured to generate, supply, and/or deliver gas (e.g., pressurized air) toward patient 11 via mask apparatus 14. For example, gas delivery system 12 may comprise a device capable of generating pressurized air (e.g., a ventilator, CPAP system, or BiPAP system), a wall outlet through which pressurized air may be supplied (e.g., in a hospital or clinic), one or more tanks of compressed gas, a compressor, or any other suitable source of pressurized or non-pressurized gas. As used herein, the term "gas" may refer to any one or more gases and/or vaporized substances suitable to be delivered to and/or from a patient via one or more breathing orifices (e.g., the nose and/or mouth), such as air, nitrogen, oxygen, any other component of air, $CO_2$, vaporized water, vaporized medicines, and/or any combination of two or more of the above, for example.

The term "patient" may refer to any person or animal that may receive breathing assistance from system 10, regardless of the medical status, official patient status, physical location, or any other characteristic of the person. Thus, for example, patients may include persons under official medical care (e.g., hospital patients), persons not under official medical care, persons receiving care at a medical care facility, persons receiving home care, persons not yet receiving care, etc. In certain embodiments, the term "patient" may refer to any person or animal that has not yet received breathing assistance and/or other type of care, but may have a facial seal fabricated or selected for such patient in accordance with the present disclosure, for subsequent use in a breathing assistance system.

Mask apparatus 14 may be generally configured to deliver gas supplied by gas delivery system 12 to patient 11 and/or to remove exhaust gas away from patient 11. Mask apparatus 14 may include one or more gas delivery conduits 20, a patient interface assembly 22 communicatively coupled to at least one conduit 20, and/or headgear 24 for securing mask apparatus 14 to the patient's head, which may include securing patient interface apparatus 22 against the patient's face. Mask apparatus 14 may include any other components, e.g., a forehead support system, one or more adjustment systems, and/or a gas exhaust system, each of which may be separate from, or partially or fully integrated with, one or more other components of mask apparatus 14.

As discussed in greater detail with reference to FIG. 1, patient interface assembly 22 may include a facial seal 30 coupled to a seal support 32. In some embodiments, facial seal 30 may be releasably coupled to seal support 32. As discussed below, seal support 32 may define an opening and may include a support member connection portion extending at least substantially around the opening, and facial seal 30 may include a facial seal connection portion that may be deformed to mate with the support member connection portion to releasably and sealably couple facial seal 30 to seal support 32.

Facial seal 30 may be configured to provide a seal around at least one breathing passageway of patient 11, e.g., the patient's nose and/or mouth. In some embodiments, facial seal 30 may comprise a nasal interface that fits around the patient's nose. In other embodiments, facial seal 30 may comprise a mouth interface that fits around the patient's mouth. In other embodiments, facial seal 30 may comprise a full face interface that fits around the patient's nose and mouth. Facial seal 30 may be a single, integrated component, or may include multiple components coupled together. All or portions of facial seal 30 may be formed from one or more flexible or deformable materials. Face interfacing side 44 of facial seal 30 may be formed from a flexible or deformable material (e.g., deformable plastic or rubber) to provide an effective and comfortable seal against the face of patient 11. In some embodiments, the facial seal may be fabricated using rapid prototyping (e.g., selective laser sintering, fused deposition modeling, three-dimensional laser printing, or laminated object manufacturing). In the same or alternative embodiments, the facial seal may be fabricating using a subtractive manufacturing technique (e.g., laser ablation, chemical removal, and mechanical cutting).

Seal support 32 may comprise any component of mask apparatus 14, such as a mask shell, a support member, a frame member, a base member, a connection member, an arm member, or a conduit, for example. In the example embodiment shown in FIG. 1, seal support 32 comprises a mask shell or frame that includes headstrap connection portions for receiving headstraps for securing facial seal 30 against the patient's face. Seal support 32 may be a single, integrated component, or may include multiple components coupled together.

Mask apparatus 14 may be coupled to gas delivery system 12 by connection system 16. Connection system 16 may include any one or more conduits (e.g., one or more flexible hoses) for communicating gas from gas delivery system 12 to mask apparatus 14. In some embodiments, connection system 16 may be coupled to one or more gas delivery conduits 20 of mask apparatus 14. When assembled, breathing assistance system 10 may define one or more gas delivery passageways from gas delivery system 12 to patient 11, passing through connection system 16, gas delivery conduit(s) 20, patient interface assembly 22, and/or one or more other components of system 10. Such passageways may be used to deliver gas from gas delivery system 12 to patient 11. In addition, in some embodiments, gas delivery conduits 20 and/or connection system 16 may include or define one or more passageways for communicating exhaled gas away from patient 11.

Figure 2:
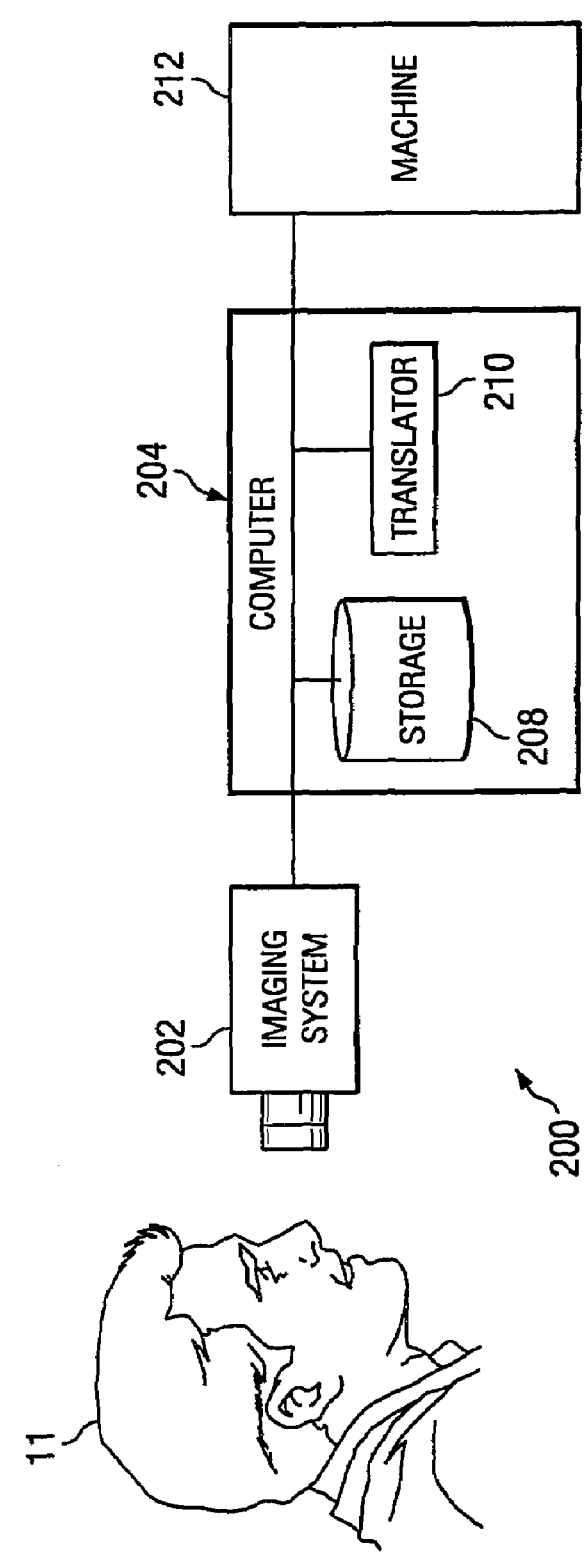
FIG. 2 illustrates an example system for fabricating a facial seal, according to some embodiments of the disclosure.

FIG. 2 illustrates an example system 200 for fabricating facial seal 30, according to some embodiments of the disclosure. System 200 may include an imaging system 202, a computer 204, and a fabrication machine 212.

Imaging system 202 may include any system or apparatus operable to capture one or more images of at least a portion of a patient's face. For example, as discussed in greater detail with reference to FIGS. 3A-3D, imaging system 202 may comprise a laser scanning system 202*a* (see FIG. 3A), a stereo photography system 202*b* (see FIG. 3B), or a tactile imaging system (see FIGS. 3C and 3D).

Computer 204 may include any system or apparatus operable to translate images captured by imaging system 202 into data representative of three-dimensional structures of objects imaged by imaging system 202. As used in this disclosure, "computer" may include, without limitation, any instrumentality or aggregate of instrumentalities operable to compute, classify, process, transmit, receive, retrieve, originate, switch, store, display, manifest, detect, record, reproduce, handle, or utilize any form of information, intelligence, or data for business, scientific, control, entertainment, or other purposes. For example, computer 204 may be a personal computer, a personal digital assistant, a consumer electronic device, a server, a network storage device, a computer residing in a kiosk or stand-alone machine (e.g., for imaging a patient's face and/or fabricating a custom mask), or any other suitable device and may vary in size, shape, performance, functionality, and price. Computer 204 may include memory, one or more processing resources such as a central processing unit (CPU), or hardware or software control logic. Additional components of computer 204 may include one or more storage devices 208, one or more communications ports for communicating with external devices as well as various input and output (I/O) devices, such as a keyboard, a mouse, and a video display. Computer 204 may also include one or more buses operable to transmit communication between the various hardware components.

In the embodiment shown in FIG. 2, computer 204 may comprise a storage device 208 and/or a translator 210. Translator 210 may be any system or apparatus operable to translate images captured by imaging system 202 into data representing three-dimensional structures of objects imaged by imaging system 202. In some embodiments, translator 210 and/or another component of computer 204 may be operable to translate the data representing the three-dimensional structure of an object into a set of instructions that may be executable by a machine operable to fabricate facial seal 30. Storage 208 may be any tangible computer-readable storage medium operable to store data or instructions, for example, data representing three-dimensional structures of objects imaged by imaging system 202 and/or instructions translated from such data. Storage 208 may include, for example, a network attached storage device, a file server, a direct access storage device (e.g., a disk drive), a sequential access storage device (e.g., a tape drive), and/or any other suitable device for storing data or instructions.

Machine 212 may include any apparatus or system operable to fabricate a facial seal 30 in accordance with the present disclosure. In one embodiment, machine 212 may comprise a rapid prototyping machine operable to fabricate at least a portion of facial seal 30, e.g., using selective laser sintering, fused deposition modeling, three-dimensional laser printing, laminated object manufacturing, and/or any other rapid prototyping technique. In the same or alternative embodiments, machine 212 may comprise a machine utilizing a subtractive manufacturing technique (e.g., mechanical cutting, chemical removal and/or laser ablation) operable to create a three-dimensional pattern in at least a portion of facial seal 30. Using one or more the these techniques, and/or any other suitable technique, machine 212 may fabricate facial seal 30 including a three-dimensional pattern corresponding to a three-dimensional structure of the patient's face, as imaged by imaging system 202 and translated by translator 210.

In operation, imaging system 202 may capture one or more images of at least a portion of the face of patient 11. Translator 210 and/or another component of computer 204 may translate the one or more images into a set of data representing a three-dimensional structure of the imaged portion of the patient's face. In some embodiments, translator 210 and/or another component may also translate the set of data into a set of instructions executable by a machine operable to fabricate facial seal 30. In the same or alternative embodiments, computer 204 may store the set of data or the set of instructions in storage 208. Machine 212 may execute the set of instructions to fabricate facial seal 30 based at least on the set of data and/or the set of instructions.

Although FIG. 2 depicts using a single computer 204 to translate images into data and translate data into instructions, it is understood that any number of computers may be used to fabricate facial seal 30 in accordance with the present disclosure. For example, system 200 may include a first computer 204 to translate images into data, and a second computer 204 to translate data into instructions. In the same or alternative embodiments, a first computer 204 may store images, translated data, and/or translated instructions in storage 208, which may be retrieved, used, and/or stored by a second computer 204.

Figure 3A:
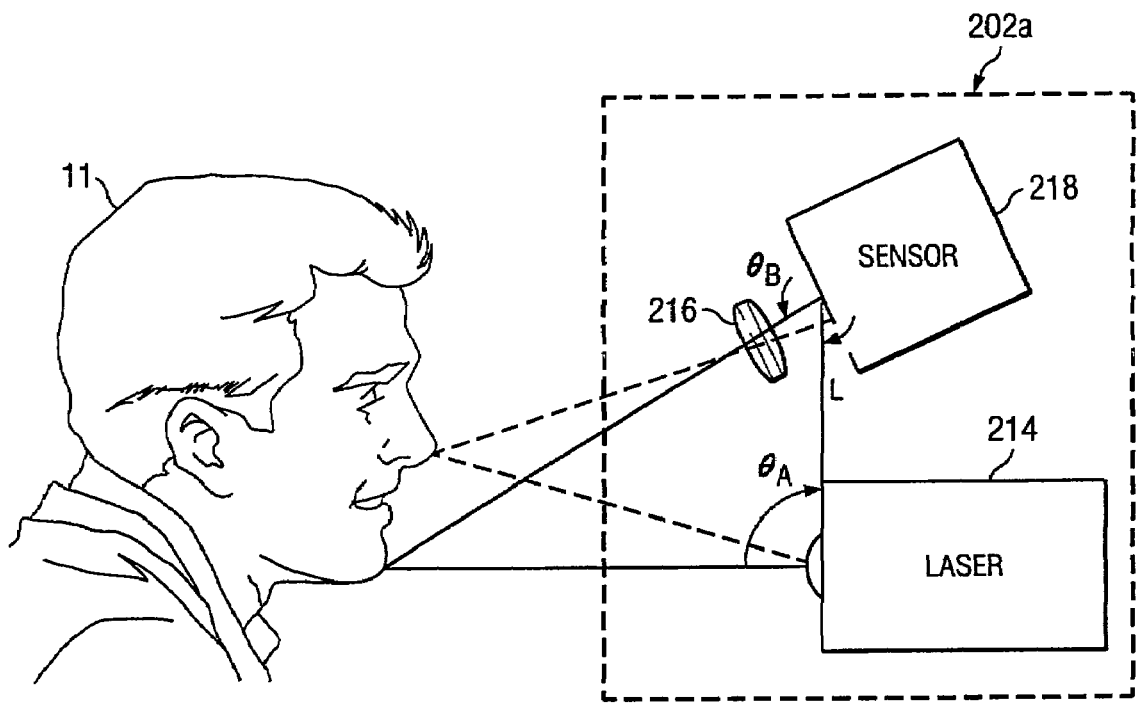
FIGS. 3A-3D illustrate example imaging systems for capturing images of a patient's face for use in fabricating a facial seal, according to some embodiments of the disclosure.

FIG. 3A illustrates an example imaging system 202a for capturing one or more images of at least a portion of the patient's face using triangulation laser scanning, according to certain embodiments of the disclosure. System 202a may include laser 214, lens 216 and sensor 218. Laser 214 may include any optical source that emits photons in a coherent beam. For example, laser 214 may comprise a gas laser (e.g., a helium-neon laser, a carbon dioxide laser, an argon-ion laser, a carbon monoxide laser, a transverse electrical discharge in gas at atmospheric pressure laser, a helium-silver laser, a neon-copper laser, and/or other metal ion laser), a chemical laser (e.g., a hydrogen fluoride laser and/or a deuterium fluoride laser), an excimer laser, a solid-state laser, semiconductor laser or a dye laser. Lens 216 may be any system or apparatus operable to focus light reflected from patient 11 onto sensor 218. Sensor 218 may comprise any system or apparatus operable to sense, record, detect and/or playback an image. For example, sensor 218 may comprise a digital recorder, a camera, a charge coupled device (CCD) camera, and or a position sensitive detector (PSD). Sensor 218 may further be interfaced with a computer (e.g., computer 204) that includes processing resources.

In operation, laser 214 may transmit a beams of light towards patient 11. Light reflected from the face of patient 11 may then be focused by lens 216 onto sensor 218. Depending on the relative location of the various facial features of patient 11, light detected by sensor 218 will appear at various locations in sensor 218's field of view. Thus, sensor 218 and laser 214 may form a triangle with each point on the patient's face. In addition, the length L between sensor 218 and laser 214 may be known, as well as the angle $\Theta_A$ at the corner of the triangle corresponding to laser 214. The angle $\Theta_B$ of the corner of the triangle corresponding to sensor 218 may be determined by recording the location of the reflection onto sensor 218. With these three data (L, $\Theta_A$, and $\Theta_B$), the shape and size of the triangle can be determined using basic mathematic principles. Thus, by scanning a portion of the patient's face, the three-dimensional contour of the portion can be determined. In some embodiments, laser 214 may emit a dot of light that is swept or scanned across the desired portion of the patient's face, and sensor 218 may capture an image of the desired portion by recording the locations of reflection of the dot. In other embodiments, a laser stripe, instead of a single laser dot, may be swept across the desired portion to expedite the image capturing process.

Figure 3B:
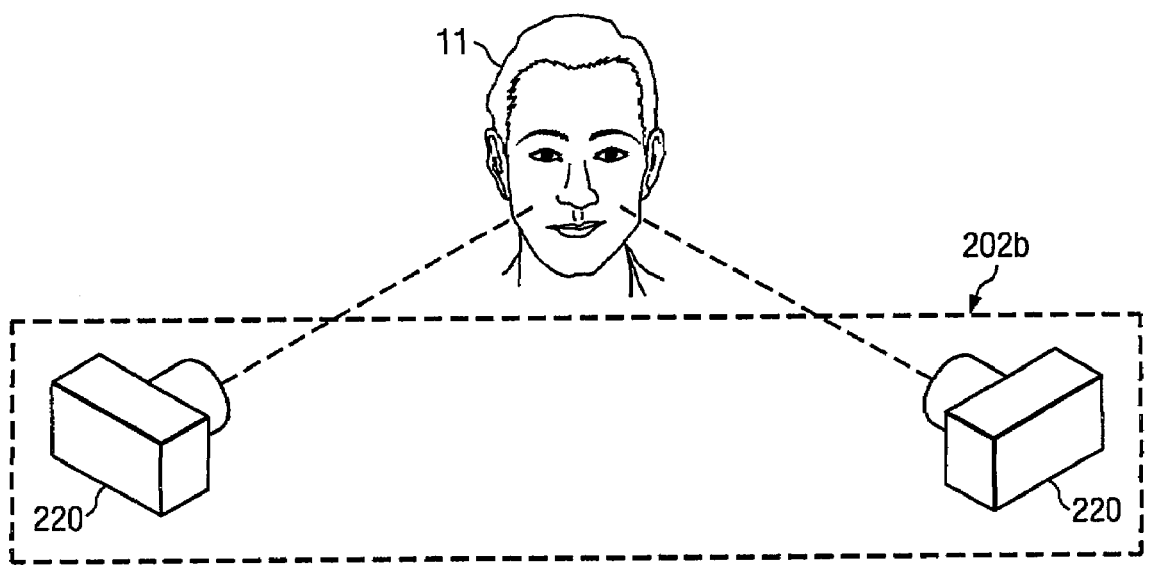

FIG. 3B illustrates an example imaging system 202b for capturing one or more images of at least a portion of the face of a patient 11 using stereo photography, according to certain embodiments of the disclosure. Imaging system 202b may include two or more sensors 220. Similar to sensor 218, sensors 220 may comprise any system or apparatus operable to sense, record, detect and/or playback an image. For example, sensors 220 may comprise a digital recorder, a camera, a charge coupled device (CCD) camera, and or a position sensitive detector (PSD). Sensor 220 may further be interfaced with a computer (e.g., computer 204) that includes processing resources. In operation, each sensor 220 may be located a particular distance from each other sensor 220. Each sensor 220 may capture an image of at least a portion of the patient's face. The differences between the images captured by each sensor may be analyzed (for example, by computer 204) to determine the three-dimensional contour of a particular portion of the patient's face.

Figure 3C:
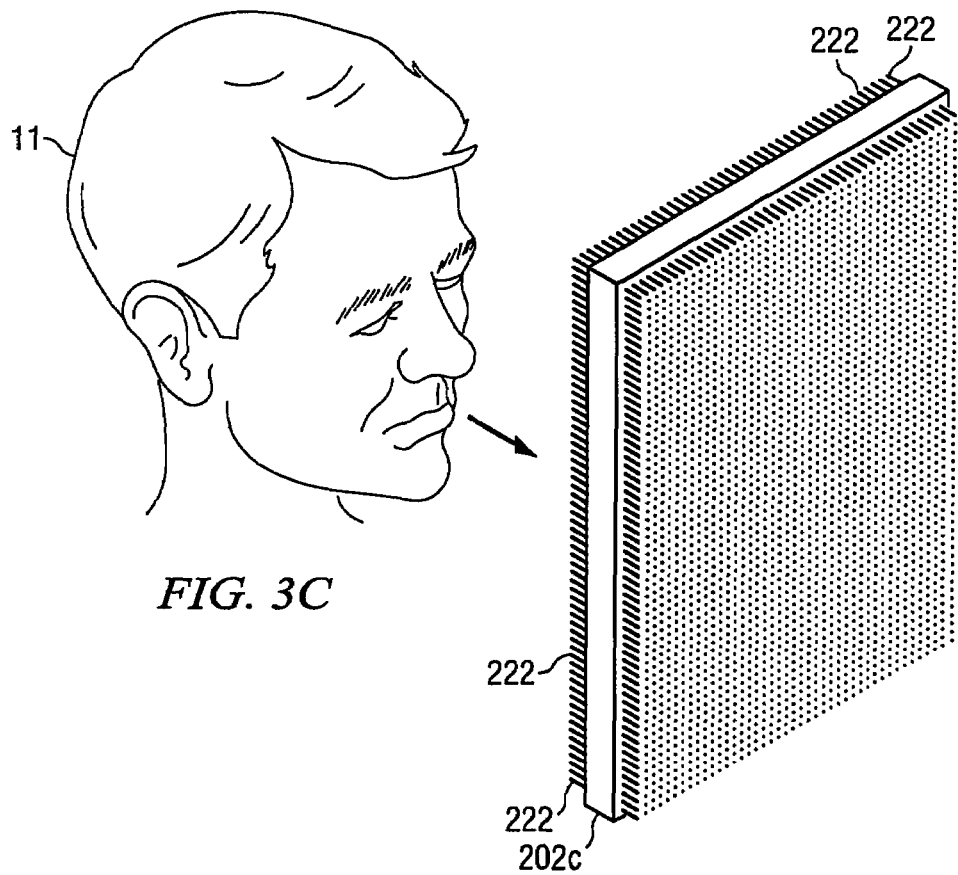
Figure 3D:
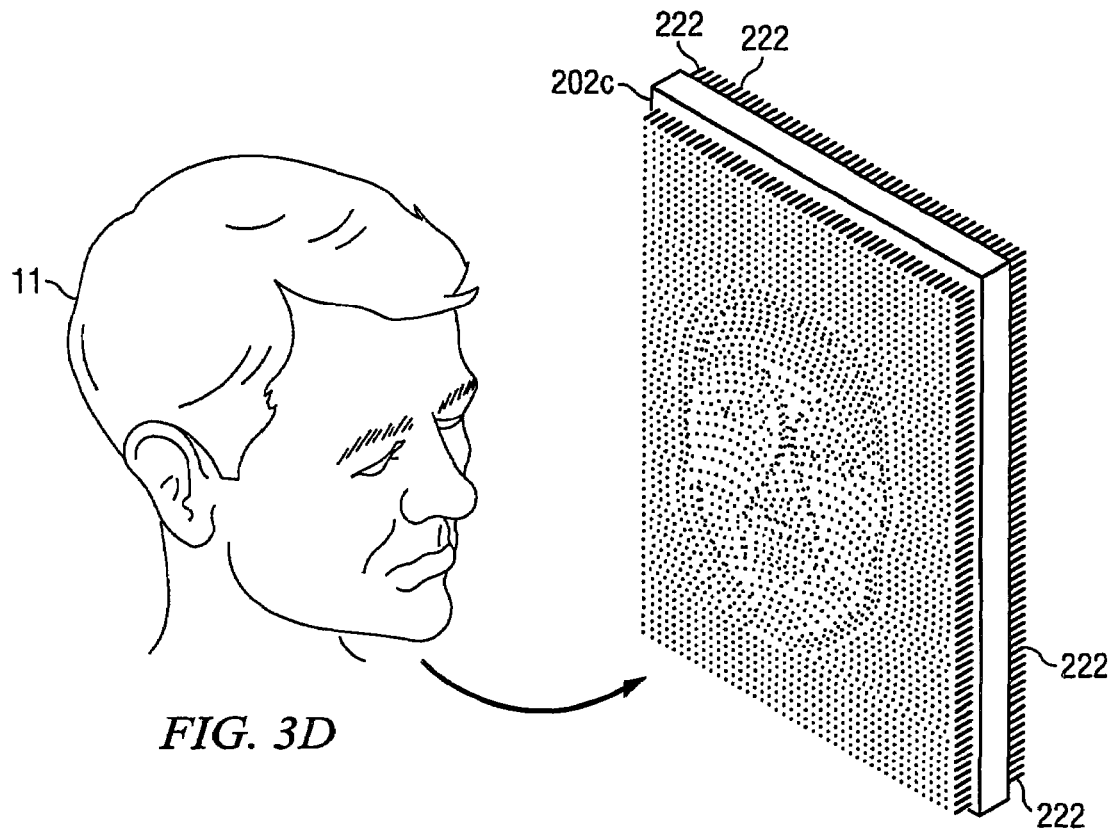

FIGS. 3C and 3D illustrate an example imaging system 202c for capturing one or more images of at least a portion of the face of a patient 11 using tactile imaging, according to certain embodiments of the disclosure. Imaging system 202c may include a plurality of substantially parallel movable pins 222 arranged in an array or grid. In operation, a surface of imaging system 202c substantially perpendicular to pins 222 may placed against the patient's face. In response to contacting the various features of the patient's face, a number of pins 222 may slide and/or become displaced in a direction substantially parallel to pins 222, as depicted in FIG. 3D. By analyzing the displacement of each pin 222 (for example, by computer 204), the three-dimensional contour of a desired portion of the patient's face can be determined.

Although FIGS. 3A-3D depict particular techniques for capturing images of a patient's face, it is understood that any imaging system suitable for capturing images or other three-dimensional representation of a patient's face may be used in accordance with the disclosure. For example, imaging system 202 may utilize laser interferometry, structured illumination, range from focus, time-of-flight, and/or moire contouring. In addition, imaging system 202 may utilize tactile imaging techniques other than those discussed above with reference to FIGS. 3C and 3D. For example, in addition to using an array of substantially parallel pins as depicted in FIGS. 3C and 3D, imaging system may utilize any suitable system or apparatus in which a patient's face creates a displacement of material that can be analyzed to determine the three-dimensional contour of a patient's face, including, without limitation, a mold, putty, gel or other deformable material.

Figure 4A:
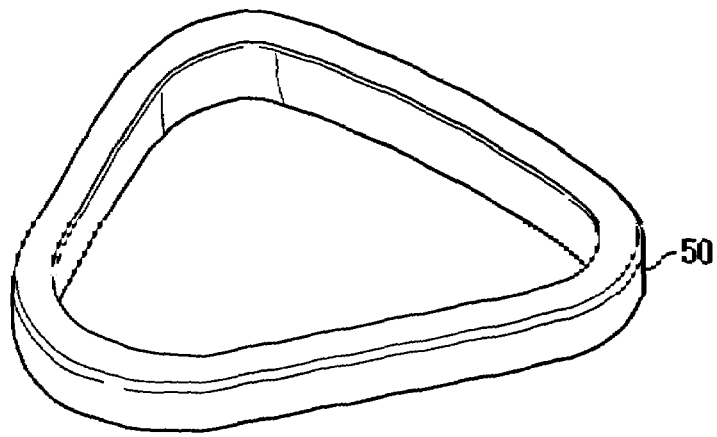
FIGS. 4A-4C illustrate various stages of fabrication of a facial seal using rapid prototyping, according to one embodiment of the disclosure.
Figure 4B:
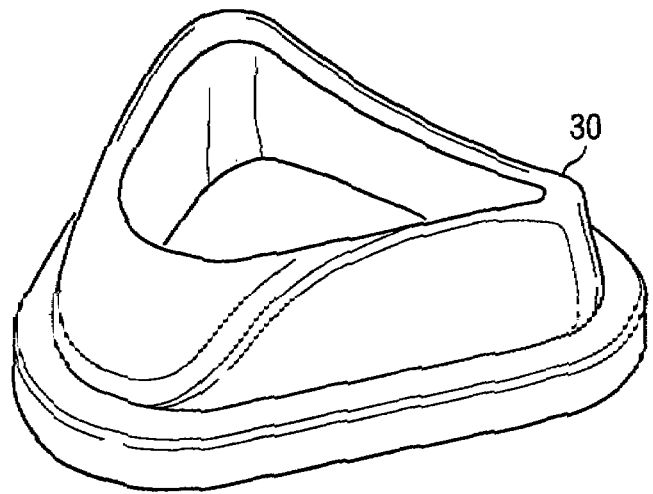
Figure 4C:
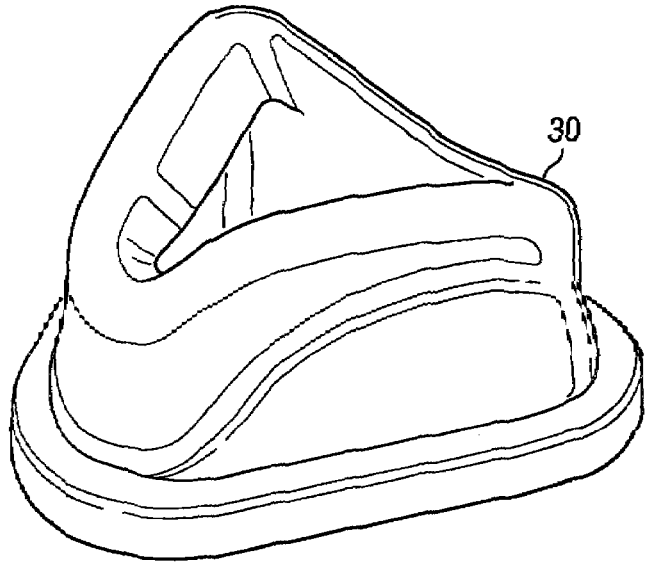

FIGS. 4A-4C illustrate various stages of fabrication of a facial seal 30 using rapid prototyping, according to one embodiment of the disclosure. As discussed above, facial seal 30 may be fabricated using a rapid prototyping machine (e.g., machine 212) using any suitable rapid prototyping technique, including without limitation, selective laser sintering, fused deposition modeling, three-dimensional laser printing, and/or laminated object manufacturing. For example, machine 212 may, based on data or instructions translated by computer 204, fabricate facial seal 30 in a series of cross-sections. Machine 212 may comprise a laser which may selectively fuse small particles of plastic, silicone, rubber, other suitable flexible or deformable material, and/or other material suitable for use in facial mask 30 by scanning, on the surface of a bed of suitable particles, cross-sections generated (e.g., by computer 204) from a three-dimensional description of facial mask 30, thus fusing the particles to create facial mask 30. FIG. 4A depicts partially manufactured facial seal 30 at a given time during manufacture using rapid prototyping. FIG. 4B depicts partially manufactured facial seal 30 at a later time during manufacture, after a plurality of small particles corresponding to a plurality of cross-sections have been fused to facial seal 30. FIG. 4C depicts facial seal 30 after small particles corresponding to each cross-section of facial seal 30 have been fused.

FIGS. 5A and 5B illustrate two stages of fabrication of facial seal 30 using a subtractive manufacturing technique, according to one embodiment of the disclosure. As discussed above, facial seal 30 may be fabricated by a machine using any suitable subtractive manufacturing technique, including without limitation, mechanical cutting (e.g., with a blade), chemical reaction (e.g., dissolving material via chemical reaction), or laser ablation. For example, machine 212 may, based on data or instructions translated by computer 204, fabricate facial seal 30 by removing material from an unprocessed or "blank" facial seal. In one embodiment, machine 212 may comprise a laser operable to selectively ablate undesired portions of a facial seal blank, e.g., facial seal blank 50 depicted in FIG. 5A, to create a facial seal 30 with a desired three-dimensional structure, as depicted in FIG. 5B. In another embodiment, machine 212 may comprise a chemical application apparatus operable to selectively remove undesired portions of a facial seal blank, e.g., facial seal blank 50 depicted in FIG. 5A, to create a facial seal 30 with a desired three-dimensional structure, as depicted in FIG. 5B. In yet another embodiment, machine 212 may comprise a mechanical cutting device, e.g., a blade, operable to selectively remove undesired portions of a facial seal blank, e.g., facial seal blank 50 depicted in FIG. 5A, to create a facial seal 30 with a desired three-dimensional structure, as depicted in FIG. 5B.

FIG. 6 illustrates an example method 300 for fabricating a facial seal, according to some embodiments of the disclosure. At step 302, imaging system 202 may capture one or more images of the patient's face. Imaging system 202 may utilize any suitable technique to capture the one or more images, e.g., laser scanning as described in FIG. 3A, stereo photography as described in FIG. 3B, and/or tactile imaging as described in FIGS. 3C and 3D. At step 304, translator 210 and/or another component of computer 204 may translate the one or more captured images into a set of data representing a three-dimensional structure of at least a portion of the patient's face. At step 306, translator 210 and/or another component of computer 204 may translate the set of data into a set of instructions executable by machine 212 to fabricate facial seal 30. At step 308, machine 212 may fabricate facial seal 30 based at least on the set of instructions and/or the set of data. Machine 212 may fabricate seal 30 using a rapid prototyping technique (e.g., selective laser sintering, fused deposition modeling, three-dimensional laser printing, and/or laminated object manufacturing) as depicted in FIGS. 4A-4C, a subtractive technique (e.g., mechanical cutting, laser ablation and/or chemical removal) as depicted in FIGS. 5A and 5B, or any other known or suitable technique.

FIG. 7 illustrates an example method 320 for selecting a facial seal from a plurality of sample facial seals, according to some embodiments of the disclosure. At step 322, a sample of test subjects may be selected, each subject sharing one or more demographic characteristics. In some embodiments, the one or more common demographic characteristics may comprise race, ethnicity, geographic origin, height, weight, and/or age. At step 324, an imaging system (e.g., imaging system 202) may capture one or more images of each test subject's face. Imaging system 202 may utilize any suitable technique to capture the one or more images, e.g., laser scanning as described in FIG. 3A, stereo photography as described in FIG. 3B, and/or tactile imaging as described in FIGS. 3C and 5D.

At step 326, translator 210, another component of computer 204, or another computer may translate the one or more captured images of the test subjects' faces into a set of sample data. At step 328, computer 210 or other suitable component may determine a three-dimensional structure of a sample facial seal based at least on the set of sample data relating to the selected sample of test subjects. At step 329, machine 212 may fabricate the sample facial seal based on the three-dimensional structure determined at step 328. The sample facial seal may have characteristics and functionality similar to facial seal 30. Machine 212 may fabricate the sample facial seal using a rapid prototyping technique (e.g., selective laser sintering, fused deposition modeling, three-dimensional laser printing, and/or laminated object manufacturing) as depicted in FIGS. 4A-4C, a subtractive technique (e.g., mechanical cutting, laser ablation and/or chemical removal) as depicted in FIGS. 5A and 5B, or any other known or suitable technique. At step 330, a determination may be made as to whether it is desirable to sample additional test subjects or fabricate additional sample facial seals. If more samples are desired, method 320 proceeds again to step 322. Otherwise, method 320 may proceed to 332.

Thus, by repeating steps 322 through 328 numerous times, one may obtain a plurality of sets of sample data, as well as fabricate numerous sample facial seals, each such sample facial seal specifically designed for individuals with one or more common demographic characteristics. For example, if it is desired to create a facial seal intended to fit average-sized African-American males between the ages of 25 and 50, a group of subjects meeting the demographic criteria for the sample may be selected at step 322, and a sample facial seal intended to substantially conform to the faces of the sample subjects may be fabricated at step 328. Accordingly, rather than creating a fully custom facial seal for a patient as discussed above with respect to method 300, a patient may be fitted with "semi-custom" facial seal that permits an approximate fit based on the patient's demographic characteristics. In addition, the availability of numerous sample facial seals representing individuals of various demographic backgrounds may facilitate automatic selection of an appropriate sample facial seal by imaging and characterization of a patient's face, as discussed below.

At step 332, imaging system 202 may capture one or more images of a patient's face. Imaging system 202 may utilize any suitable technique to capture the one or more images, e.g., laser scanning as described in FIG. 3A, stereo photography as described in FIG. 3B, and/or tactile imaging as described in FIGS. 3C and 3D. At step 334, translator 210, another component of computer 204, and/or another computer may translate the one or more captured images of the patient's face into a set of facial data representing a three-dimensional structure of the portion of the patient's face. At step 336, a computer (e.g., computer 204) may compare the set of facial data to the plurality of sets of sample data created in steps 322 through 328. At step 338, a facial seal is selected (e.g., selected by computer 204 or other computer) from one of the sample facial seals based at least on the comparison made at step 336. Any suitable means may be used to select the desired facial seal. For example, the selected facial seal may be the facial seal that provides a best fit approximation of the three-dimensional contours of the patient's face of the available sample facial seals. Such "best fit" determination may be made based on various factors, e.g., the differences between the set of patient data and each set of sample patient data corresponding to various points or locations on the patient's face.

It will be appreciated that while the disclosure is particularly described in the context of breathing assistance systems, the apparatuses, techniques, and methods disclosed herein may be similarly applied in other contexts. Additionally, it should be understood that various changes, substitutions and alterations can be made herein without departing from the spirit and scope of the disclosure as illustrated by the following claims.

What is claimed is:

1. A method for selecting a facial seal for use in a breathing assistance system, comprising:
   obtaining a plurality of three-dimensional contour data sets, each three-dimensional contour data set comprising data from images of three-dimensional exterior facial contours of a plurality of test subjects having a common demographic characteristic, such that each three-dimensional contour data set corresponds to one or more different demographic characteristics;
   using a computer, processing each three-dimensional contour data set to generate a characteristic three-dimensional structure for a sample facial seal corresponding to that three-dimensional contour data set;
   for each three-dimensional contour data set, fabricating a sample facial seal based on the characteristic three-dimensional structure generated based on that three-dimensional contour data set, such that a plurality of sample facial seals are fabricated, each having a different shape corresponding to one or more different demographic characteristics;
   obtaining a set of data representing a three-dimensional structure of an exterior surface contour of a patient's face; and
   automatically selecting a particular one of a plurality of sample facial seals having different shapes, the particular facial seal selected to substantially conform to the patient's face based at least on the set of facial data, including:
      using a computer, automatically comparing the set of facial data to the plurality of three-dimensional contour data sets, each three-dimensional contour data set representing a three-dimensional structure of one of the plurality of sample facial seals; and
      using the computer, automatically selecting the particular facial seal from the plurality of sample facial seals based at least on the comparison.

2. A method according to claim 1, wherein obtaining data from images of three-dimensional exterior facial contours of a plurality of test subjects comprises using an image capturing technique selected from a group consisting of laser scanning, stereo photography, and tactile imaging.

3. A method according to claim 1, wherein a facial seal comprises a mask cushion.

4. A method according to claim 1, wherein the one or more demographic characteristics are selected from a group consisting of race, ethnicity, geographic origin, height, weight, and age.

5. A method for making sample facial seals comprising:
   selecting a sample of test subjects having a common demographic characteristic;
   capturing an image of a three-dimensional structure of an exterior surface contour of a face of each test subject;
   translating the images into a set of sample data corresponding to the common demographic characteristic;
   storing the set of sample data in a database;
   using a computer, processing the sample data set from the plurality of test subjects in order to automatically generate a characteristic three-dimensional structure for a sample facial seal based at least on the set of sample data; and
   fabricating the sample facial seal based on the generated characteristic three-dimensional structure such that the sample facial seal is designed for a plurality of individuals having the demographic characteristic.

6. A method, comprising:
   obtaining a plurality of three-dimensional contour data sets, each three-dimensional contour data set comprising data from images of three-dimensional exterior facial contours of a plurality of test subjects having a common demographic characteristic, such that each three-dimensional contour data set corresponds to one or more different demographic characteristics;
   using a computer, processing each three-dimensional contour data set to generate a characteristic three-dimensional structure for a sample facial seal corresponding to that three-dimensional contour data set; and for each three-dimensional contour data set, fabricating a sample facial seal based on the characteristic three-dimensional structure generated based on that three-dimensional contour data set, such that a plurality of sample facial seals are fabricated, each having a different shape corresponding to one or more different demographic characteristics;

using the plurality of sample facial seals to provide multiple options for selection of a particular sample facial seal for a patient.

* * * * *